United States Patent [19]
Burger et al.

[11] Patent Number: 5,493,051
[45] Date of Patent: Feb. 20, 1996

[54] LIFIBROL AND ITS USE

[75] Inventors: Artur Burger; Anita Lettenbichler, both of Innsbruck, Austria; Fritz Stanislaus, München, Germany; Arnim Laicher, München, Germany; Karl Schwitzer, München, Germany; Axel Woschina, Poing, Germany

[73] Assignee: Klinge Pharma GmbH, Munich, Germany

[21] Appl. No.: 235,525

[22] Filed: Apr. 29, 1994

[30] Foreign Application Priority Data

Apr. 29, 1993 [DE] Germany ............ 43 14 175.7

[51] Int. Cl.⁶ .................................................. C07C 65/00
[52] U.S. Cl. ................................................... 562/473
[58] Field of Search .................... 562/473, 401; 560/64

[56] References Cited

U.S. PATENT DOCUMENTS 5,266,721 11/1993 Reiter et al. ................. 560/64

FOREIGN PATENT DOCUMENTS 0133935 12/1987 European Pat. Off. .

OTHER PUBLICATIONS

Chem Abst. 118: 168821 1992.

Thermomicroscopy of organic compounds, Kuhnert–Brandstätter, Elsevier, pp. 422 and 423.

Primary Examiner—Paul J. Killos
Attorney, Agent, or Firm—Sughrue, Mion, Zinn, Macpeak & Seas

[57] ABSTRACT

A new modification of Lifibrol is described with a melting point of 132° C.–138° C. particularly from 134° C.–136° C. and a primary peak in an IR spectrum at a wave number of 3,200–3,400, preferably 3,250–3,350. The new modification of Lifibrol (modification II) is distinguished in that it allows for good crystallization and, therefore, can be formulated without problems on a large industrial scale for tablets of acceptable size and high stability.

12 Claims, 7 Drawing Sheets

LIFIBROL AND ITS USE

The invention concerns the modification II of the lipid-reducing pharmaceutical preparation Lifibrol(INN), 4-(4'-tert.butylphenyl)- 1-(4'carboxyphenoxy)-2-butanol. Lifibrol is a new cholesterol synthesis inhibitor which effectively reduces cholesterol and LDL-cholesterol.

Lifibrol, which is described in EP-0133935, is odorless and has a bad taste. At first, Lifibrol was obtained in the modification I form in which the active substance is crystallized from acetone, chloroform, carbon tetrachloride, or xylene. Modification I also forms through precipitation from alkaline solutions with the help of acids or through precipitation with a miscible nonsoluble medium such as petroleum ether from benzolic solution.

The production process of Lifibrol should also be feasible on an industrial scale. For this purpose, the product must exist in a form which can be filtered and lightly dried without difficulty. Due to the intense adhesivness of modification I, the damp crystalizate is filtered with extreme difficulty. A single filtration operation lasts several days, which is difficult to tolerate in the scope of a rational Lifibrol synthesis.

With respect to the production of a pharmaceutical formulation, there exists a particular desire for the development of a coated tablet. The necessary single dosages for clinical potency should be tested in the scope of dose-determination studies of up to 800 mg Lifibrol. This above limit is derived from pre-clinical studies. This 800 mg Lifibrol dosage should be realized by the dosage of one single coated tablet. In this regard, one is orientated, among other things, by the contents of active substance per drug of the lipid-reducing pharmaceutical already found on the market, which is to be drawn from Table 1.

TABLE 1

Contents of Active Substance in Selected Lipid-reducing Finished pharmaceutical Preparations

| INN | Dosage (mg) | Weight of Drug | Contents of Active Substance (%) |
| --- | --- | --- | --- |
| Clofibrat | 500 | 743 | 67.3 |
| Benzafibrat | 200 | 310 | 64.5 |
| Simvastatin | 10 | 100 | 10.0 |
| Etofyllinclofibrat | 500 | 653 | 76.6 |
| Gemfibrozil | 450 | 740 | 60.8 |
| Etofibrat | 300 | 872 | 34.4 |
| Lovastatin | 20 | 200 | 10.0 |
| Pravastatin-Na | 10 | 200 | 5.0 |
| Mod. I formulation (Lifibrol) | 200 | 700 | 28.6 |
| Mod. II formulation (Lifibrol) | 200 | 280 | 71.4 |
| Mod. I corresp. formulation (Lifibrol) | 300 | 1050 | 28.6 |
| Mod. II corresp. formulation (Lifibrol) | 800 | 1120 | 71.4 |

Separate from these technical problems, the goal of the formulation of coated tablets of acceptable size (for example, oblong tablets 20.0×9.2 mm) has not been accomplished in any case. This had the consequence that, in clinical studies, the 800 mg dosage was achieved by the dosage of two coated tablets, each of which contained 300 mg Lifibrol, and a coated tablet with 200 mg Lifibrol. For later dosages of up to 800 mg this divided dosage would not be tolerated on the grounds of patient compliance.

The problem according to the invention is to make available a method in order to industrially produce Lifibrol active substance in an acceptable manner and formulate coated tablets of acceptable size (maximal 20.0×9.2 mm) with a high content of active substance (minimal 70%) and secured stability behavior, even when stored under stress conditions. Furthermore, on the basis of the previously acquired clinical test results, Lifibrol coated tablets of different crystal structures and formulations should be as to their extent bio-equivalent to each other.

Figure 1:
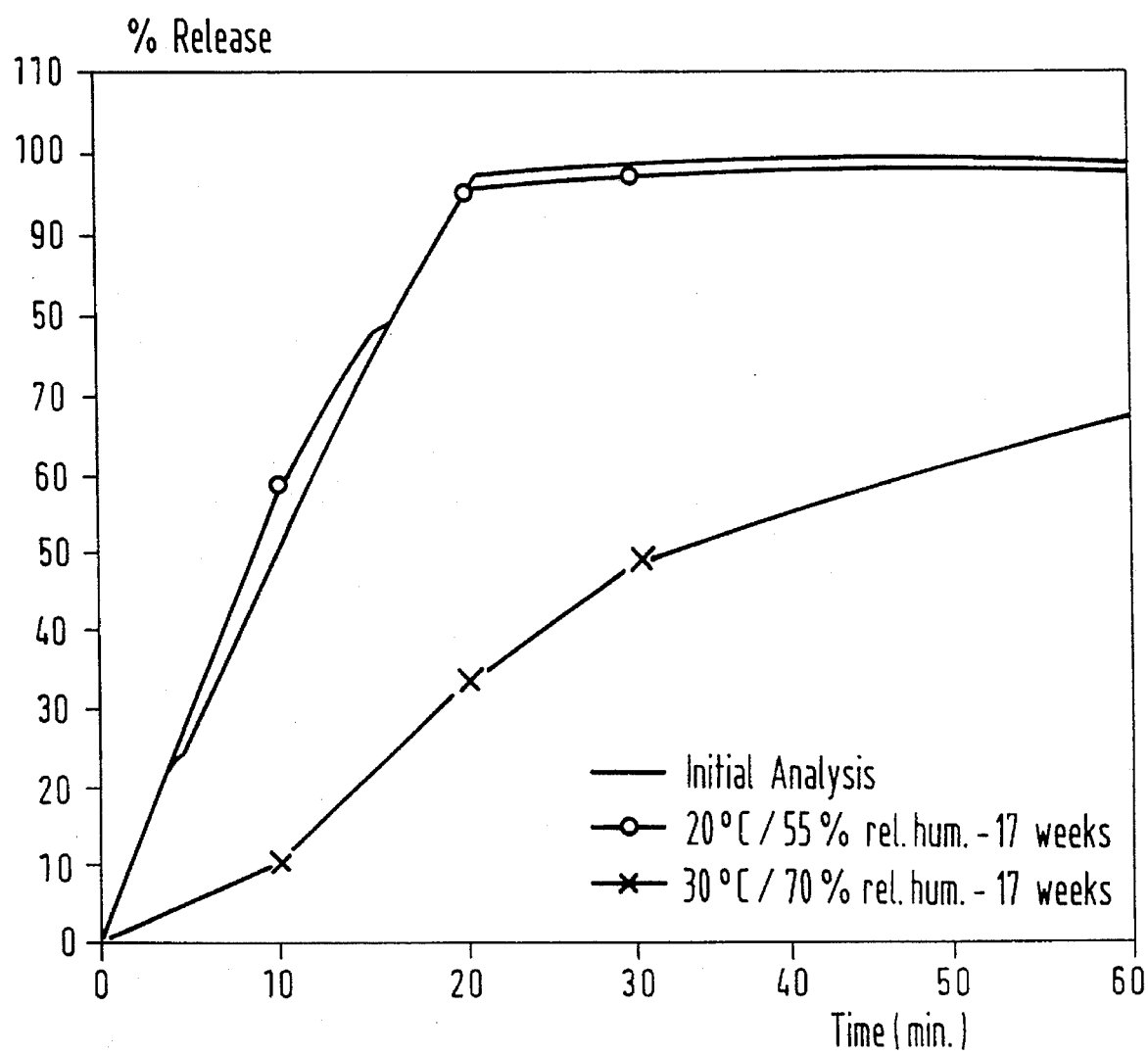
FIG. 1: In vitro release of Lifibrol from coated tablets of modification I
Figure 2:
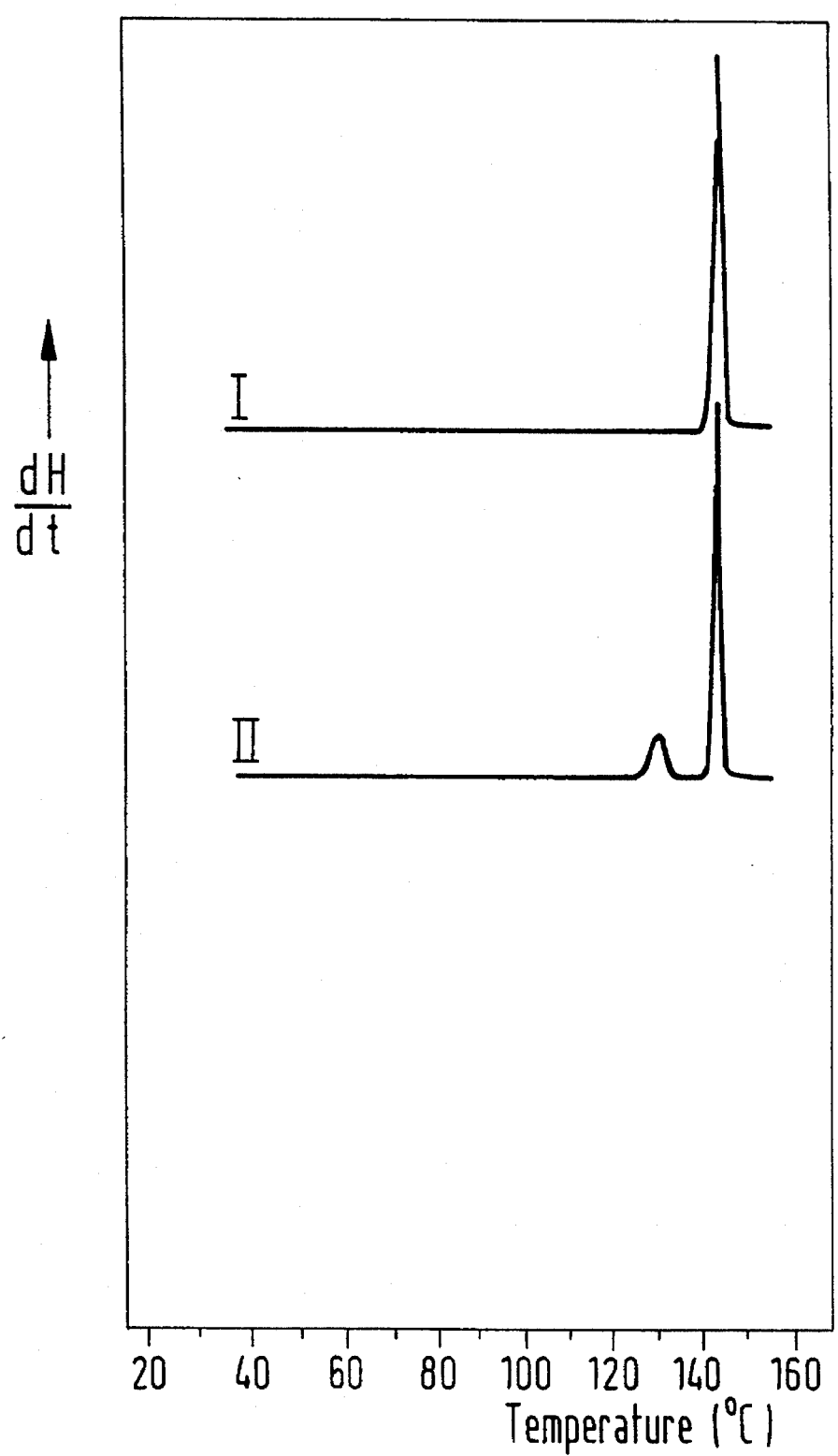
FIG. 2: Melt diagrams of modification I and modification II of Lifibrol

Surprisingly, those Lifibrol crystals which allow for the formulation of coated tablets with a high content of active substance are obtained, for example, by stirring (magnetic stirrer, room temperature) of suspended Lifibrol of modification I in water or water-ethanol or water-ethanol-mixtures or also by crystallization out of methanol, ethanol, or ethyl acetate or by precipitation from alcoholic solutions with water. Microscopically, one recognizes rhombohedrical crystal nuclei (approx. 10–25 μm in size) which exhibit low interference colors in polarized light. Upon heating in a thermal microscope at 125° C. or higher, one can identify a transformation-caused color change, or rather, a loss of color, in an optically polarized dark field. Melting follows nonhomogeneously at 135° C. and at 139° C. to 141° C. The last region corresponds to the melting point of modification I. For this, refer to FIG. 2.

Figure 3:
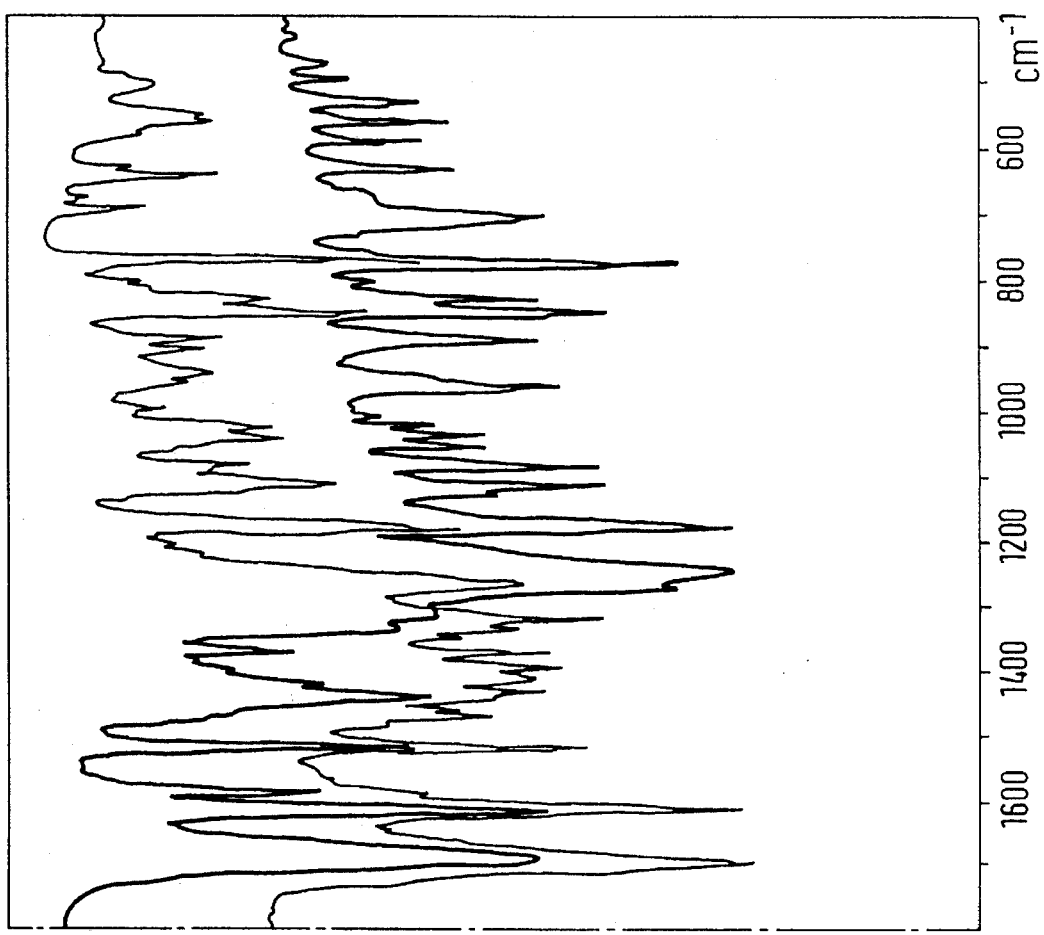
FIG. 3: IR spectrum of modification I and modification II of Lifibrol
Figure 3:
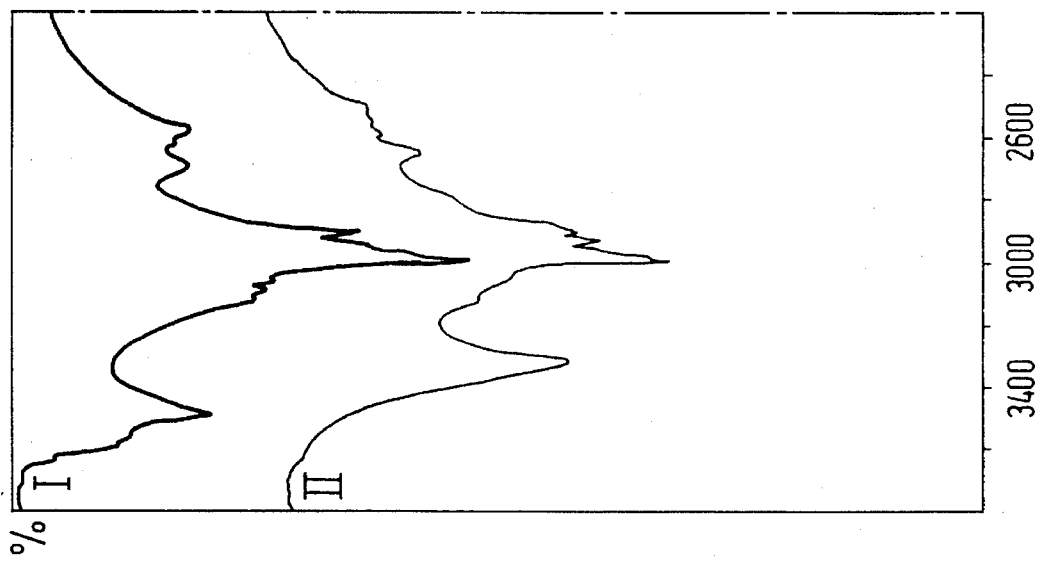

By using IR spectroscopy, modification I clearly differs from the modification of Lifibrol according to the invention, which is denoted in the following as modification II. The primary peak of modification II appears first at 3,300 cm$^{-1}$, the carboxyl peak at 1,700 cm$^{-1}$, and the hydroxyl band at 1,250 cm$^{-1}$ is clearly shifted in comparison to form I. Further differences lie at 1,060, 960, 630, and 540 cm$^{-1}$. For this, refer to the IR spectra in FIG. 3.

Figure 4:
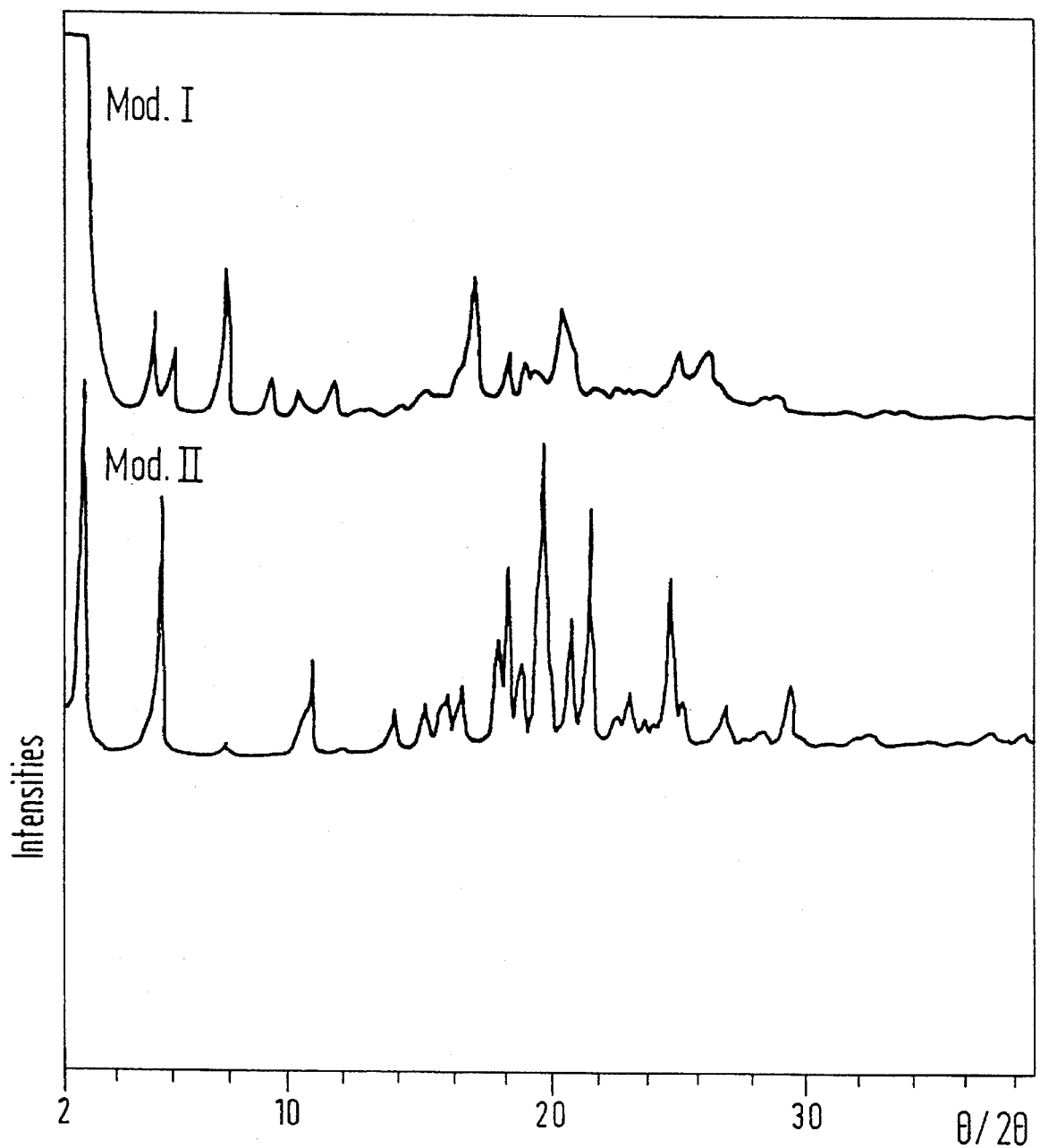
FIG. 4: X-ray diffraction of modification I and modification II of Lifibrol
Figure 5:
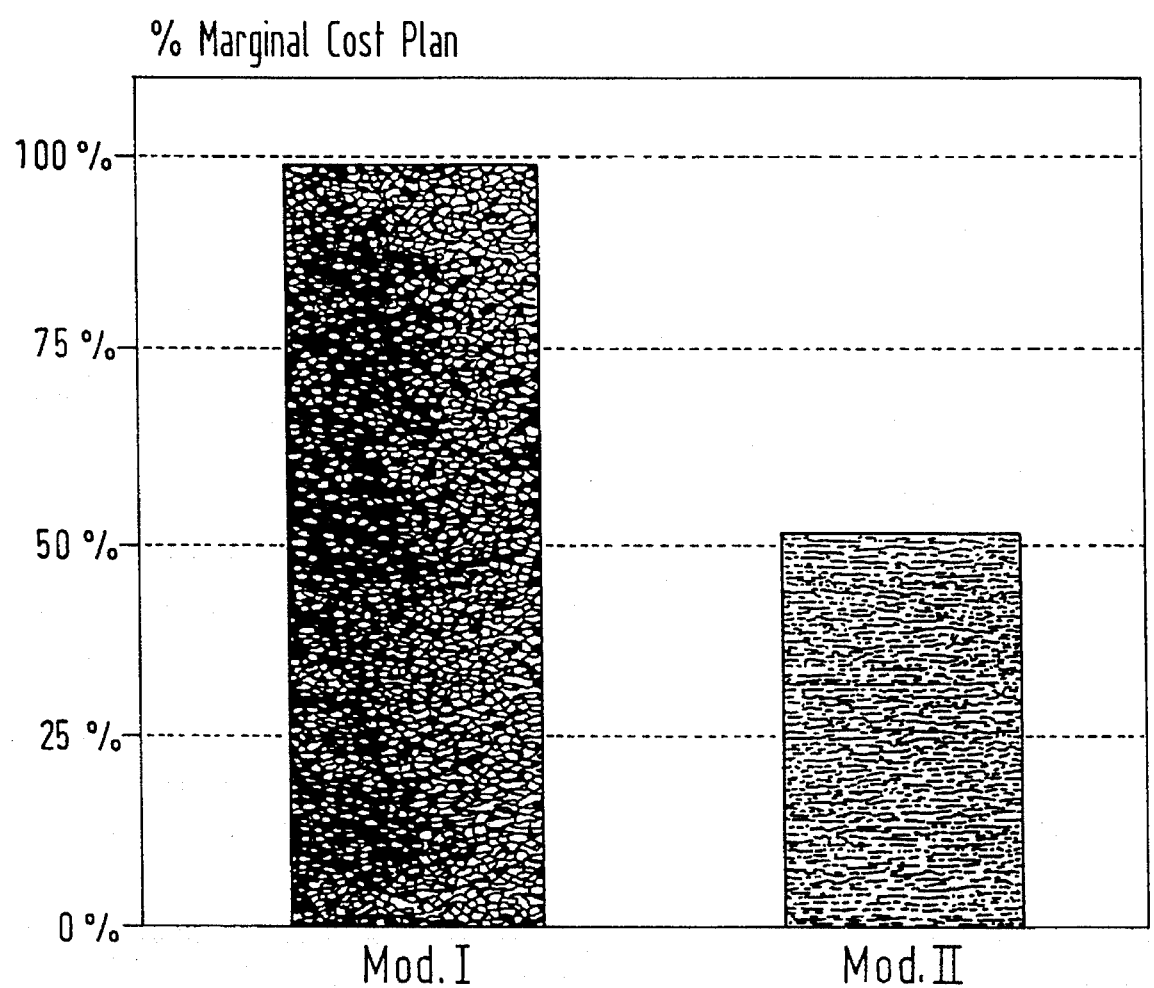
FIG. 5: Marginal cost plan (without active substance costs) of Lifibrol

By using the method of x-ray diffractometry, modification II shows the sharpest reflection bands, whereas few sharp bands are identified with modification I, which infers a loose degree of order. The characteristic interplanar spacing and relative intensities are listed for comparison in the following Table 2, whereas characteristic x-ray diffractograms follow from FIG. 4.

TABLE 2

Interplanar Spacing d (A) and Relative Intensities (I) of Characteristic X-ray interferences of Lifibrol

| Mod. I | | Mod. II | |
|---|---|---|---|
| d | I (%) | d | (I %) |
| 34.79 | 100.00 | 34.80 | 100.00 |
| 17.39 | 2.6 | 16.56 | 35.3 |
| 15.36 | 4.6 | 8.48 | 6.6 |
| 11.60 | 3.0 | 8.25 | 12.6 |
| 9.60 | 1.9 | 6.47 | 6.5 |
| 8.54 | 1.8 | 5.96 | 7.5 |
| 7.75 | 1.9 | 5.67 | 8.4 |
| 6.43 | 1.7 | 5.49 | 10.3 |
| 6.07 | 2.6 | 5.04 | 15.3 |
| 5.39 | 9.8 | 4.91 | 24.4 |
| 4.94 | 5.1 | 4.80 | 12.2 |
| 4.74 | 4.7 | 4.75 | 12.1 |
| 4.64 | 4.8 | 4.53 | 39.3 |
| 4.39 | 7.8 | 4.27 | 17.6 |
| 4.29 | 5.6 | 4.12 | 32.5 |
| 3.93 | 3.0 | 3.84 | 8.5 |
| 3.56 | 4.2 | 3.58 | 23.0 |
| 3.42 | 3.4 | 3.31 | 6.9 |
| | | 3.04 | 9.2 |

Further characteristic values for both modifications such as, for comparison, the true densities are shown in the following Table 3.

TABLE 3

Characteristic Values of Modification I and II of Lifibrol

| Modifications | I | II |
|---|---|---|
| Melting Point (TM) (°C.) | 142 | 135 |
| Stability RT | I < II | II > I |
| Habit | small plates | rhombohedron |
| Heat of melting (kJ/mol) ± 95% confidence level | 38.11 ± 0.16 | 49.11 (calculated) |
| Heat of Transition to Mod. I ± 95% conf. level (kJ/mol) (°C.) | | +11.00 ± 0.21 123–130 |
| Transition Point (TM) (°C.) | | 70–85 |
| Density (g/cm$^3$) | 1.178 ± 0.003 | 1.209 ± 0.004 |
| First Peak in IR Spectrum Wave number (cm$^1$) | 3,470 | 3,300 |

Based on the described principles in the literature (Thermomicroscopy of Organic Compounds, Kuhnert-Brandstätter, Elsevier, p. 422 ff) according to which in a comparison of the two modifications the one that is more stable, has a higher density, and has a primary band in the IR spectrum at a lower frequency (lower wave number) is unequivocally modification II, which is also gathered from Table 3.

Modification I and modification II of Lifibrol differ in their pH solubility profiles. This is clearly shown in the following Table 4.

TABLE 4 pH-solubility Profile of Different Modifications of Lifibrol at 37° C. after 3 Hours in Selected Weak Buffer Systems

| | pH 1.2 | pH 6.8 | pH 7.5 |
|---|---|---|---|
| Modification I | 0.72 mg/ 1000 ml | 229 mg/ 1000 ml | 750 mg/ 1000 ml |
| Modification II | 0.48 mg 1000 ml | 129 mg 1000 ml | 627 mg 1000 ml |

On the ground of the aforementioned characterized adhesive tendency, a much higher portion of auxiliary material was required for the total formulation for the production of coated tablets according to formulation Example A compared to the production of coated tablets of modification II according to formulation Example B. The latter also clearly has an effect on the production of coated tablets (here, based on a coated tablet with a dosage of 200 mg Lifibrol). The corresponding pressure parameters for the different Lifibrol modifications are referred to in Table 5. The following dimensions are based on the coated tablets of the different modifications:

Modification I—23×9.5×6.5 mm or 17 mm round domed, tablet weight 1,430 mg;

Modification II—17×8×5.5 mm or 12 mm round domed, tablet weight 580 mg.

Figure 7:
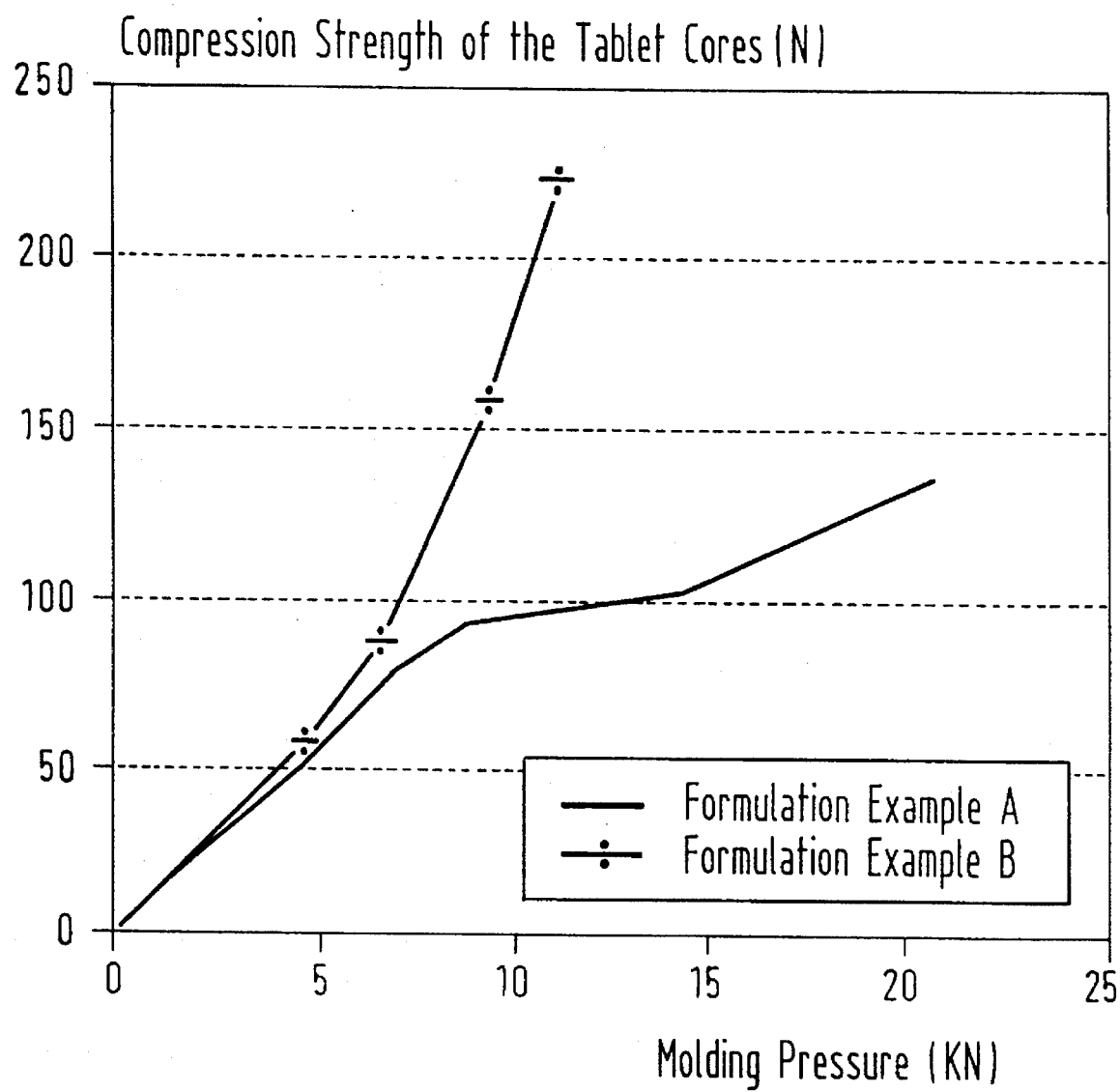
FIG. 7: Hardness-molding pressure profile Due to the intensive adhesivness of modification I, a relatively large amount of auxiliary material (70%) was necessary. Even with this large amount of auxiliary material, it was extremely difficult to obtain tablet cores with sufficient compression strength for later film coating. Above all, the production on fast running, high-capacity tablet compressing machines is extremely difficult because of the shortened pressurization time, in comparison to a eccentric tablet compressing machine, regarding the compression strength of the tablet cores. Separate from these technical difficulties with respect to the filtration of the crystalizates and the difficult compressibility, coated tablets produced in this manner exhibit insufficient stability behavior because, for example, in the primary packaging material Alu-PVC/PVDC under the storage conditions of 30° C./70% rel. humidity (ambient humidity), the Lifibrol release rate is significantly reduced in comparison to the initial value. It is supposed that a change in the crystal habit was the cause for this since the characteristic values for the disintegration of the coated tablets did not change over the storage time.

As deduced from FIG. 7, the hardness-molding pressure profile in the case of the production of tablet cores according to formulation Example B shows a much more favorable trend than that of the production of tablet cores according to formulation Example A.

The following Table 5 shows that the pressure parameters for the production of tablet cores according to formulation Example B are more favorable than those for the production of tablet cores according to formulation Example A, which is decidedly important from the viewpoint of non-problematic coating of tablet cores in a large facility.

TABLE 5

Pressure Parameters for the Lifibrol Modifications from Formulation Examples A and B

| Formulation | according to Formulation Ex A | according to Formulation Ex. B |
|---|---|---|
| Top Force Molding Pressure (KN) | 8.7 | 9.2 |
| Power Transmission | 0.5 | 0.75 |
| Residual Force (N) | 1250 | 425 |
| Discharging Force (N) | 950 | 488 |

The curve of the dependence of the compression strength of the tablet cores on the molding pressure is presented in FIG. 7.

In vitro release of Lifibrol

In the following Tables 6 and 7, the in vitro release of modification I or modification II of Lifibrol at different pH values (pH 7.5 and 6.8) are presented.

TABLE 6

In vitro Release of Lifibrol at pH 7.5 (0.05 M $KH_2PO_4$)
1 Tablet in 1000 ml Buffer - Paddle - 100 rpm - 37° C.

| Sample Taken after minute: | Tablet Mod. I. 100 mg Crude mat.: d' = 6.5 μm Required wt: 350 mg Batch: 06901206 mg/1000 ml dissolved | Tablet Mod. II 100 mg Crude mat.: d' = 21 μm Required wt: 350 mg Batch: 06901209 mg/1000 ml dissolved |
|---|---|---|
| 5 | x = 96.2<br>SD = 3.96<br>SDR = 4.1% | x = 93.0<br>SD = 1.45<br>SDR = 1.5% |
| 10 | x = 100.7<br>SD = 1.06<br>SDR = 1.0% | x = 100.6<br>SD = 3.76<br>SDR = 3.7% |
| 20 | x = 102.7<br>SD = 1.68<br>SDR = 1.6% | x = 102.6<br>SD = 0.5<br>SDR = 0.4% |
| 30 | x = 101.9<br>SD = 0.85<br>SDR = 0.8% | x = 103.0<br>SD = 0.4<br>SDR = 0.3% |
| 40 | x = 103.5<br>SD = 1.4<br>SDR = 1.3% | x = 103.7<br>SD = 1.04<br>SDR = 1.0% |
| 50 | x = 103.0<br>SD = 1.51<br>SDR = 1.4% | x = 103.0<br>SD = 0.61<br>SDR = 0.5% |
| 60 | x = 102.7<br>SD = 1.08<br>SDR = 1.0% | x = 102.7<br>SD = 0.75<br>SDR = 0.7% |
| 120 | x = 102.6<br>SD = 1.4<br>SDR = 1.3% | x = 103.2<br>SD = 1.56<br>ISDR = 1.5% |
| 180 | x = 102.6<br>SD = 0.1<br>SDR = 0.0% | x = 103.1<br>SD = 0.58<br>SDR = 0.5% |
| 240 | x = 103.8<br>SD = 1.1<br>SDR = 1.0% | x = 102.6<br>SD = 1.43<br>SDR = 1.4% | x = average value, N = 3.

By comparison of the above values, in vitro release of modification I and modification II of Lifibrol exhibit equivalent behavior.

TABLE 7

In vitro Release of Lifibrol at pH 6.8 (0.05 M $KH_2PO_4$)
1 Tablet in 1000 ml Buffer - Paddle - 100 rpm - 37° C.

| Sample Taken after minute: | Tablet Mod I. 100 mg Crude mat.: d' = 6.5 μm Required wt: 350 mg Batch: 06901206 mg/1000 ml dissolved | Tablet Mod. II 100 mg Crude mat.: d' = 21 μm Required wt: 350 mg Batch: 06901209 mg/1000 ml dissolved |
|---|---|---|
| 5 | x = 63.8<br>SD = 2.12<br>SDR = 3.3% | x = 58.4<br>SD = 1.59<br>SDR = 2.7% |
| 10 | x = 78.0<br>SD = 1.53<br>SDR = 1.9% | x = 74.5<br>SD = 2.99<br>SDR = 4.0% |
| 20 | x = 86.9<br>SD = 0.52<br>SDR = 0.6% | x = 84.0<br>SD = 3.35<br>SDR = 3.9% |
| 30 | x = 91.7<br>SD = 1.06<br>SDR = 1.1% | x = 88.2<br>SD = 3.53<br>SDR = 4.0% |
| 40 | x = 94.1<br>SD = 0.92<br>SDR = 0.9% | x = 89.7<br>SD = 3.04<br>SDR = 3.3% |
| 50 | x = 95.7<br>SD = 0.32<br>SDR = 0.3% | x = 91.3<br>SD = 3.2<br>SDR = 3.5% |
| 60 | x = 96.2<br>SD = 1.31<br>SDR = 1.3% | x = 91.3<br>SD = 4.07<br>SDR = 4.4% |
| 120 | x = 99.2<br>SD = 0.86<br>SDR = 0.8% | x = 95.2<br>SD = 4.65<br>SDR = 4.8% |
| 180 | x = 99.6<br>SD = 0.4<br>SDR = 0.4% | x = 95.8<br>SD = 4.2<br>SDR = 4.3% |
| 240 | x = 100.7<br>SD = 2.6<br>SDR = 2.5% | x = 97.3<br>SD = 2.03<br>ISDR = 2.0% | x = average value, N = 3.

From the above pH values, an equivalent in vitro release rate is observed for both modifications of Lifibrol.

Comparison of the Bio-availability 18 probands were subjected to 2 coated tablets each according to either model formulation Examples A or B in a bio-availability comparison.

Figure 6:
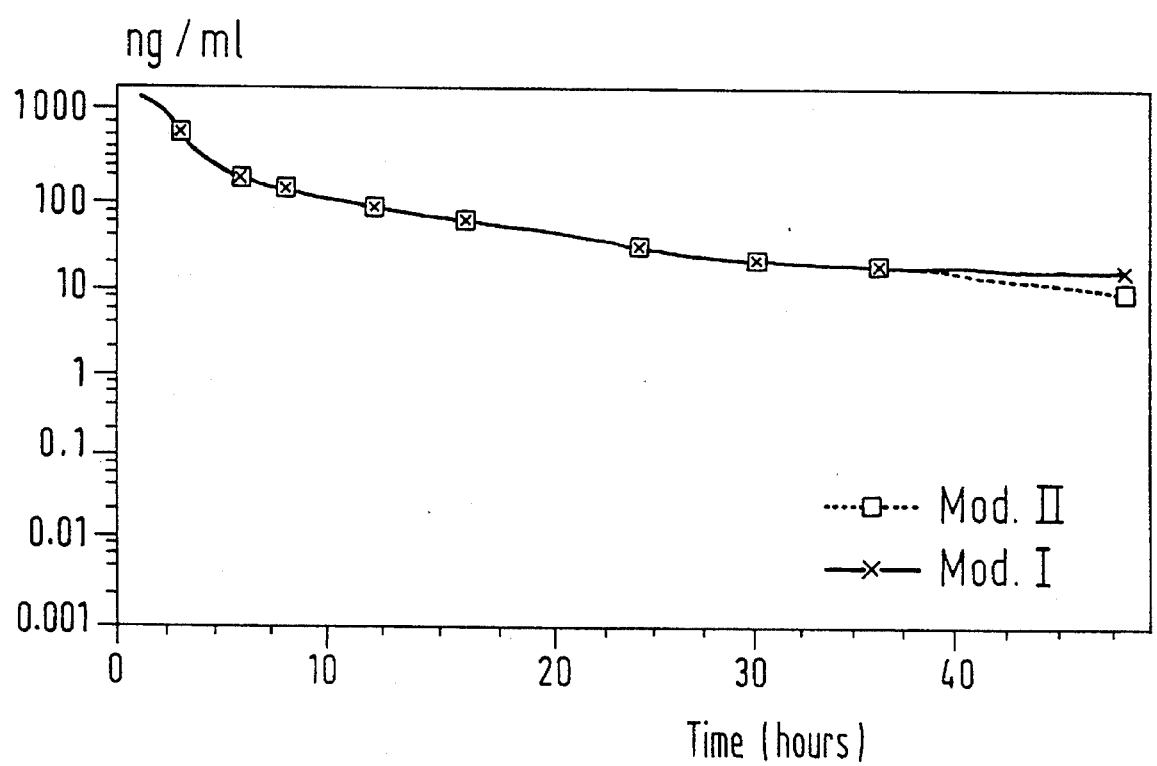
FIG. 6: Comparison of the average Lifibrol concentration in plasma from 18 probands after a dosage of 400 mg of Lifibrol in the form of modification I or modification II

No difference between the two formulations is recognized in a comparison of the Lifibrol-plasma average values as to their extent, which is shown in FIG. 6.

Obviously, the auxiliary material which is necessary for the production of the drugs according to the invention is not restricted to the filling material named in the formulation Examples.

Production of Lifibrol-modification II from the ester precursor 4-[4-(4'-tert.butylphenyl)-2-hydroxybutoxy]-methyl benzoate

EXAMPLE 1

35 parts of 4[-4-(4'-tert.butylphenyl)-2-hydroxybutoxy]-methyl benzoate (produced according to EP 0133935) are heated by refluxing with a solution of 7 parts sodium hydroxide in 120–130 parts of methanol for several hours. The solution is acidified with ca. 22 parts of concentrated HCl. After cooling to room temperature, 4-(4'-tert.butylphenyl)-1-( 4'-carboxyphenoxy)-2-butanol-(crude) is separated. 23 parts of 4-(4'-tert.butylphenyl)-1-(4'carboxyphenoxy)-2-butanol-(crude) are dissolved at reflux temperature in 90 parts methanol and 10 parts water. The crystallization of modification II followed by cooling to room temperature. The precipitate is filtered by vacuum and washed with a mixture of 9 parts methanol and 1 part water, and dried in a vacuum.

Colorless crystals with a melting point of 135° C. are obtained. The yield amounted to 20.3 g (59.4%).

Analysis values: $C_{21}H_{26}O_4$ (342.4) Mol. Wt. 342 (mass-spectrometrically determined by means of Electron impact ionization (70 eV)

IR spectrum (KBr) v(OH) 3,300 $cm^{-1}$ v(C=O) 1,690 $cm^{-1}$ $^1$H-NMR spectrum ($CDCl_3$): 1.30 s (9) ($\underline{CH_3})_3$C 1.73 to 2.17 m (2) Ar$CH_2\underline{CH_2}$ 2.63 to 3.03 m (2) Ar$\underline{CH_2}CH_2$ 3.80 to 4.27 m (3) C$\underline{H}$C$\underline{H_2}$O 6.67 to 8.20 m (10) Aromatic O$\underline{H}$ COO$\underline{H}$ Production of Lifibrol-modification II by conversion of Lifibrol-modification I.

EXAMPLE 2

15 parts Lifibrol-modification I are suspended in 30 parts methanol and stirred at room temperature for 60 hours.

Subsequently, the precipitate is filtered, and after vacuum drying at 40° C., 11.8 parts of colorless crystals of Lifibrol-modification II are obtained with a melting point of 135° C.

IR-spectra (KBr) v(OH) 3300 cm$^{-1}$, v(C=O) 1690 cm$^{-1}$.

EXAMPLE 3

5 parts Lifibrol-modification I are suspended in 30 parts methanol and stirred at room temperature for 16 hours. The precipitate is subsequently filtered, and after vacuum drying at 40° C., 1.9 parts of colorless crystals of Lifibrol-modification II are obtained with a melting point of 135° C.

IR-spectra (KBr) v(OH) 3300 cm$^{-1}$, v(C=O) 1690 cm$^{-1}$.

EXAMPLE 4

5 parts Lifibrol-modification I are dissolved in 15 parts boiling methanol and, after cooling to room temperature, crystallization ensues during 16 hours at 0° C. The precipitate is filtered, and after vacuum drying at 40° C., 4.3 parts of colorless crystals of Lifibrol-modification II are obtained with a melting point of 135° C.

IR-spectra (KBr) v(OH) 3300 cm$^{-1}$, v(C=O) 1690 cm$^{-1}$.

EXAMPLE 5

26 parts Lifibrol-modification I are solubilized in 117 parts methanol and 13 parts water by heating at reflux temperature. Crystallization follows by cooling to room temperature. Lifibrol-modification II is centrifuged and washed with a mixture of 9 parts methanol and 1 part water. After vacuum drying, 21 parts Lifibrol-modification II are obtained with a melting point of 135° C.

IR-spectra (KBr) v(OH) 3300 cm$^{-1}$, v(C=O) 1690 cm$^{-1}$.

EXAMPLE 6

5 parts Lifibrol-modification I are suspended in 20 parts ethanol and stirred for 16 hours at 25° C. The precipitate is subsequently filtered, and after vacuum drying at 40° C., 3.4 parts of colorless crystals of Lifibrol-modification II are obtained with a melting point of 135° C.

IR-spectra (KBr) v(OH) 3300 cm$^{-1}$, v(C=O) 1690 cm$^{-1}$.

EXAMPLE 7

5 parts Lifibrol-modification I are suspended in 10 parts ethanol and stirred for 24 hours at room temperature. The precipitate is filtered and, after vacuum drying at 40° C., 4.3 parts of colorless crystals of Lifibrol-modification II are obtained with a melting point of 135° C.

IR-spectra (KBr) v(OH) 3300 cm$^{-1}$, v(C=O) 1690 cm$^{-1}$.

EXAMPLE 8

5 parts Lifibrol-modification 1 are dissolved in 15 parts ethanol at reflux temperature. After cooling to room temperature, crystallization occurs during 36 hours at 0° C. The precipitate is filtered and, after vacuum drying at 40° C., 2.8 parts of colorless crystals of Lifibrol-modification II are obtained with a melting point of 135° C.

IR-spectra (KBr) v(OH) 3300 cm$^{-1}$, v(C=O) 1690 cm$^{-1}$.

EXAMPLE 9

10 parts Lifibrol-modification I are suspended in 10 parts of a mixture of 3.33 parts ethanol and 6.66 water. The viscous suspension is stirred for 20–30 hours at room temperature. The precipitate is filtered. After vacuum drying at 40° C. colorless crystals of Lifibrol-modification II are obtained with a melting point of 135° C.

IR-spectra (KBr) v(OH) 3300 cm$^{-1}$, v(C=O) 1690 cm$^{-1}$.

EXAMPLE 10

6 parts Lifibrol-modification I are dissolved at reflux temperature a mixture of 15.6 parts ethanol and 10.4 parts water. Crystallization ensues by cooling to room temperature. The precipitate is filtered and washed with 10 parts of a mixture of 6 parts ethanol and 4 parts water. After vacuum drying at 40° C., 5.6 parts of colorless crystals of Lifibrol-modification II are obtained with a melting point of 135° C.

IR-spectra (KBr) v(OH) 3300 cm$^{-1}$, v(C=O) 1690 cm$^{-1}$.

EXAMPLE 11

6 parts Lifibrol-modification I are dissolved in 18.2 parts ethanol and 7.8 parts of water are added at ca. 70° C. After cooling to room temperature the precipitate is filtered and washed with 10 parts of a mixture of 7 parts ethanol and 3 parts water. After vacuum drying at 40° C., 5.2 parts of colorless crystals of Lifibrol-modification II are obtained with a melting point of 135° C.

IR-spectra (KBr) v(OH) 3300 cm$^{-1}$, v(C=O) 1690 cm$^{-1}$.

EXAMPLE 12

6 parts Lifibrol-modification I are dissolved in 23.4 ethanol and 2.6 parts water are mixed in at ca. 70° C. After cooling to room temperature, the precipitate is filtered and washed with 10 parts of a mixture of 9 parts ethanol and 1 part water. After vacuum drying at 40° C., 4.3 parts of colorless crystals of Lifibrol-modification II are obtained with a melting point of 135° C.

IR-spectra (KBr) v(OH) 3300 cm$^{-1}$, v(C=O) 1690 cm$^{-1}$.

EXAMPLE 13

0.5 parts Lifibrol-modification I are suspended in 500 parts water. The suspension is intensively stirred at room temperature for between 20 and 30 hours, and, subsequently, the precipitate is filtered. After vacuum drying at 40° C., 0.3 parts of colorless crystals of Lifibrol-modification II are obtained with a melting point of 135° C.

IR-spectra (KBr) v(OH) 3300 cm$^{1}$, v(C=O) 1690 cm$^{1}$.

EXAMPLE 14

10 parts Lifibrol-modification I are suspended in a 100 parts water. The suspension is intensively mixed at room temperature for between 22 and 30 hours, and, subsequently, the precipitate is filtered. After vacuum drying at 40° C., 9.8 parts of colorless crystals of Lifibrol-modification II are obtained with a melting point of 135° C.

IR-spectra (KBr) v(OH) 3300 cm$^{-1}$, v(C=O) 1690 cm$^{-1}$.

EXAMPLE 15

5 parts Lifibrol-modification I are dissolved in 20 parts of boiling acetic acid ethyl ester. After cooling to room temperature, crystallization ensues during 36 hours at room temperature. The precipitate is filtered, and after vacuum drying at 40° C., 3.8 parts of colorless crystals of Lifibrol-modification II are obtained with a melting point of 135° C.

IR-spectra (KBr) v(OH) 3300 cm$^{-1}$, v(C=O) 1690 cm$^{-1}$.

EXAMPLE 16

10 parts Lifibrol-modification I are suspended in 40 parts n-propanol and stirred at room temperature for 16 hours. Subsequently, the precipitate is filtered, and after vacuum drying at 40° C., 6.8 parts of colorless crystals of Lifibrol-modification II are obtained with a melting point of 135° C.

IR-spectra (KBr) v(OH) 3300 cm$^{-1}$, v(C=O) 1690 cm$^{-1}$.

EXAMPLE 17

5 parts Lifibrol-modification I are suspended in 40 parts i-propanol and stirred at room temperature for 16 hours. Subsequently, the precipitate is filtered, and after vacuum drying at 40° C., 3.2 parts of colorless crystals of Lifibrol-modification II are obtained with a melting point of 135° C.

IR-spectra (KBr) v(OH) 3300 cm$^{-1}$, v(C=O) 1690 cm$^{-1}$.

EXAMPLE 18

5 parts Lifibrol-modification I are suspended in 50 parts toluene and stirred for 16 hours at room temperature. Subsequently, the precipitate is filtered and, after vacuum drying at 40° C., 4.2 parts of colorless crystals of Lifibrol-modification II are obtained with a melting point of 135° C.

IR-spectra (KBr) v(OH) 3300 cm$^{-1}$, v(C=O) 1690 cm$^{-1}$.

Production of Lifibrol Coated Tablets of Modification I.
formulation Example A.

|  | mg/coated tablet |
|---|---|
| I. Tablet cores |  |
| 1. Lifibrol (modification I) | 200.00 |
| 2. lactose.H$_2$O | 339.00 |
| 3. corn starch | 35.00 |
| 4. poly(1-vinyl-2-pyrrolidone) | 10.50 |
| 5. cellulose powder | 70.00 |
| 6. corn starch | 35.00 |
| 7. magnesium stearate | 3.50 |
| 8. highly dispersed silicon dioxide | 7.00 |
| II. Tablet coat |  |
| 9. methylhydroxypropylcellulose | 16.90 |
| 10. talc | 2.10 |
| 11. Macrogol 6000 | 2.10 |
| 12. titanium(IV) oxide E 171 | 8.90 |
| Film tablet weight | 730.00 |

For I (tablet core):
Modification I of Lifibrol, lactose, and corn starch are mixed and granulated with a solution of poly(1-vinyl-2-pyrrolidone) in purified water. Then, the mixture is dried and sieved, and thoroughly mixed with cellulose power, corn starch, magnesium stearate, and silicon dioxide (corresponding to components 5-and 8 and the compression molding material is molded into tablets by a rotary pelleting machine.

For II (film coating):
Methylhydroxypropylcellulose talc, Macrogol 6000, and titanium(IV) oxide are suspended or dissolved in purified water. The coating suspension is then sprayed on tablet cores with a suitable coating machine.

formulation Example B.
Production of Lifibrol Coated Tablets of Modification II.

Formulation:

|  | mg/coated tablet |
|---|---|
| I. Tablet cores |  |
| 1. Lifibrol (modification II) | 200.00 |
| 2. lactose.H$_2$O | 53.40 |
| 3. corn starch | 14.00 |
| 4. poly(1-vinyl-2-pyrrolidone) | 8.40 |
| 5. magnesium stearate | 1.40 |
| 6. highly dispersed silicon dioxide | 2.80 |
| II. Tablet coat |  |
| 7. methylhydroxypropylcellulose | 8.45 |
| 8. talc | 1.05 |
| 9. Macrogol 6000 | 1.05 |
| 10. titanium(IV) oxide E 171 | 4.45 |
| Film tablet weight | 295.00 |

For I (tablet core):
Modification II of Lifibrol, lactose, and corn starch are mixed and granulated with a solution of poly(1-vinyl-2pyrrolidone) in purified water. Then modification II of Lifibrol, lactose, and corn starch are mixed and granulated with a solution of poly(1-vinyl-2-pyrrolidone) in purified water. Then, the mixture is dried and sieved, and thoroughly mixed with magnesium stearate and silicon dioxide, and the compression molding material is molded into tablets by a rotary pelleting machine.

For II (film coating):
Methylhydroxypropylcellulose, talc, Macrogol 6000, and titanium(IV) oxide are suspended or dissolved in purified water. The coating suspension is then sprayed on tablet cores with a suitable coating machine.

We claim:

1. A modification of Lifibrol (modification II) with a melting point from 132° C. to 138° C. and primary peak in IR-spectra at a wave number from 3200 to 3400 cm$^{-1}$.

2. A modification of Lifibrol according to claim 1, wherein said melting point is from 134° C. to 136° C. and said IR-spectra primary peak wave number is 3250 to 3350 cm$^{-1}$.

3. A pharmaceutical composition comprising the modification of Lifibrol (modification II) according to claim 1 and at least one pharmaceutically acceptable additive or extender.

4. A method for the production of a well crystallized modification of Lifibrol (modification II) with a melting point from 132° C. to 138° C. and a primary peak in IR-spectra at a wave number from 3200 to 3400 cm$^{-1}$ wherein said modification is obtainable by stirring of suspended Lifibrol of an adherent consistency (modification I) in water, methanol, ethanol, a higher alcohol, toluene, a water-ethanol mixture, or a water-methanol mixture or by crystallization from methanol, ethanol, a higher alcohol, toluene, or ethyl acetate, or by precipitation from an aqueous solution of said alcohols.

5. A method according to claim 4, wherein said melting point is from 134° C. to 136° C. and said IR-spectra primary peak wave number is from 3250 to 3350 cm$^{-1}$.

6. A method according to claim 4, wherein said method comprises stirring of suspended Lifibrol in a methanol-water mixture in a weight ratio of about 9:1.

7. A method according to claim 4 wherein said method comprises stirring of suspended Lifibrol in an ethanol-water mixture in a weight ratio from 1:2 to 9:1.

8. A method according to claim 4, wherein said stirring of the suspended Lifibrol modification I is in an aqueous 0.1 to 10% by weight Lifibrol solution or suspension.

9. The pharmaceutical composition of claim 3 as a solid pharmaceutical composition.

10. The pharmaceutical composition of claim 3 as a liquid pharmaceutical composition.

11. The pharmaceutical composition of claim 9, wherein said solid pharmaceutical composition is a coated tablet.

12. The pharmaceutical composition of claim 10, wherein said liquid pharmaceutical composition is a liquid suspension.

* * * * *